(12) United States Patent
Amit et al.

(10) Patent No.: US 8,876,726 B2
(45) Date of Patent: Nov. 4, 2014

(54) PREVENTION OF INCORRECT CATHETER ROTATION

(75) Inventors: Matityahu Amit, Zur-Yigal (IL); Jaron Breitman, Timrat (IL)

(73) Assignee: Biosense Webster (Israel) Ltd. (IL)

( * ) Notice: Subject to any disclaimer, the term of this patent is extended or adjusted under 35 U.S.C. 154(b) by 38 days.

(21) Appl. No.: 13/314,359

(22) Filed: Dec. 8, 2011

(65) Prior Publication Data

US 2013/0150739 A1 Jun. 13, 2013

(51) Int. Cl.
*A61B 5/04* (2006.01)

(52) U.S. Cl.
USPC .......................................................... 600/508

(58) Field of Classification Search
None
See application file for complete search history.

(56) References Cited

U.S. PATENT DOCUMENTS

| | | | |
|---|---|---|---|
| 5,352,197 A | 10/1994 | Hammersmark et al. | |
| 5,391,199 A | 2/1995 | Ben-Haim | |
| 5,921,978 A | 7/1999 | Thompson et al. | |
| 6,239,724 B1 | 5/2001 | Doron et al. | |
| 6,332,089 B1 | 12/2001 | Acker et al. | |
| 6,484,118 B1 | 11/2002 | Govari | |
| 6,585,650 B1 | 7/2003 | Solem | |
| 6,618,612 B1 | 9/2003 | Acker et al. | |
| 6,689,089 B1 * | 2/2004 | Tiedtke et al. ................... 604/43 |
| 6,690,963 B2 | 2/2004 | Ben-Haim et al. | |
| 6,973,339 B2 | 12/2005 | Govari | |
| 7,585,273 B2 | 9/2009 | Adler et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2004/0152974 A1 | 8/2004 | Solomon | |
| 2006/0114088 A1 | 6/2006 | Shachar | |
| 2007/0103437 A1 | 5/2007 | Rosenberg | |
| 2008/0097501 A1* | 4/2008 | Blier ............................. 606/169 |
| 2010/0125253 A1* | 5/2010 | Olson et al. ................... 604/267 |
| 2010/0125276 A1* | 5/2010 | Palermo ......................... 606/80 |
| 2010/0168548 A1 | 7/2010 | Govari et al. | |
| 2010/0168557 A1* | 7/2010 | Deno et al. ................... 600/424 |
| 2010/0222859 A1 | 9/2010 | Govari et al. | |
| 2010/0305443 A1* | 12/2010 | Bartlett et al. ................ 600/443 |
| 2011/0098571 A1* | 4/2011 | Medlin et al. ................. 600/445 |

FOREIGN PATENT DOCUMENTS

| | | |
|---|---|---|
| EP | 2 415 399 A1 | 2/2012 |
| JP | 11 092847 | 4/1999 |
| WO | WO 96/05768 | 2/1996 |
| WO | WO 96/05768 A1 | 2/1996 |
| WO | WO 97/29803 A1 | 8/1997 |
| WO | WO 98/46149 A1 | 10/1998 |
| WO | WO 02/062265 A2 | 8/2002 |
| WO | WO 2004/078066 | 9/2004 |
| WO | WO 2006/116597 A2 | 11/2006 |

OTHER PUBLICATIONS

U.S Appl. No. 12/624,417, filed Dec. 20, 2009.
U.S. Appl. No. 12/975,878, filed Dec. 22, 2010.

(Continued)

*Primary Examiner* — Brian T Gedeon
*Assistant Examiner* — Ankit Tejani

(57) ABSTRACT

A method includes providing an elongated probe having a longitudinal axis and a distal end, and capable of rotation of the distal end about the longitudinal axis in mutually opposite first and second directions. While an operator manipulates the probe within a body of a patient, the rotation that is applied to the distal end is sensed automatically. An alert is issued to the operator upon sensing that the rotation is in the second direction, but not when the sensed rotation is in the first direction.

24 Claims, 3 Drawing Sheets

(56) References Cited

OTHER PUBLICATIONS

U.S. Appl. No. 12/851,085, filed Aug. 5, 2010.
U.S. Appl. No. 12/975,787, filed Dec. 22, 2010.
U.S. Appl. No. 12/649,417, filed Dec. 20, 2009.
European Search Report mailed on Mar. 20, 2013 from corresponding European Patent Application No. 12196132.0.

* cited by examiner

PREVENTION OF INCORRECT CATHETER ROTATION

FIELD OF THE INVENTION

The present invention relates generally to medical probes, and particularly to methods and systems for sensing and indicating probe rotation.

BACKGROUND OF THE INVENTION

Certain catheterization procedures, such as pulmonary vein mapping and ablation, are sometimes performed using Lasso catheters. For example, U.S. Pat. No. 6,973,339, whose disclosure is incorporated herein by reference, describes a method for electrical mapping of a pulmonary vein of a heart. The method includes introducing into the heart a catheter having a curved section and a base section, the base section having a distal end attached to a proximal end of the curved section. At a location on the curved section, a first position signal is generated having fewer than six dimensions of position and orientation information. At a vicinity of the distal end of the base section, a second position signal is generated having six dimensions of position and orientation information. The method also includes measuring, at one or more locations on the curved section, an electrical property of the pulmonary vein. Lasso catheters are also described in U.S. Patent Application Publications 2010/0168548 and 2010/0222859, whose disclosures are incorporated herein by reference.

SUMMARY OF THE INVENTION

An embodiment of the present invention that is described herein provides a method, which includes providing an elongated probe having a longitudinal axis and a distal end, and capable of rotation of the distal end about the longitudinal axis in mutually opposite first and second directions. While an operator manipulates the probe within a body of a patient, the rotation that is applied to the distal end is sensed automatically. An alert is issued to the operator upon sensing that the rotation is in the second direction, but not when the sensed rotation is in the first direction.

In some embodiments, the distal end includes a hook-shaped curve in a plane that is oriented obliquely with respect to the longitudinal axis. In an embodiment, the probe includes a lasso cardiac catheter. In a disclosed embodiment, automatically sensing the rotation includes receiving a signal from a sensor coupled to the probe, and determining the rotation based on the received signal. In another embodiment, receiving the signal includes accepting the signal from a position sensor that generates the signals responsively to an externally-generated magnetic field. In yet another embodiment, receiving the signal includes accepting the signal from an acceleration sensor that generates the signal responsively to an angular acceleration of the probe. In an embodiment, the sensor is coupled to the distal end of the probe.

In some embodiments, sensing the rotation includes measuring an impedance between at least one sensor coupled to the distal end and one or more electrodes attached to the body of the patient, and calculating the rotation based on the measured impedance. In an embodiment, issuing the alert includes displaying a visual alert on a monitor display viewed by the operator. In another embodiment, issuing the alert includes sounding an audible alarm to the operator.

In a disclosed embodiment, the method includes detecting an entanglement of the distal end with tissue in the body, and issuing a notification of the entanglement to the operator. Detecting the entanglement may include detecting a deviation of a shape of the distal end from a reference shape. In an embodiment, the probe is designated for operation in atria of a heart of the patient, and the method includes measuring a location of the probe and alerting the operator upon detecting that the probe is located in a ventricle of the heart.

There is additionally provided, in accordance with an embodiment of the present invention, apparatus including a processor and an output device. The processor is connected to an elongated probe that has a longitudinal axis and a distal end and is capable of rotation of the distal end about the longitudinal axis in mutually opposite first and second directions. The processor is configured to automatically sense the rotation that is applied to the distal end while an operator manipulates the probe within a body of a patient, and to issue an alert upon sensing that the rotation is in the second direction, but not when the sensed rotation is in the first direction. The output device is configured to present the alert to the operator.

The present invention will be more fully understood from the following detailed description of the embodiments thereof, taken together with the drawings in which:

DETAILED DESCRIPTION OF EMBODIMENTS

Overview

When a physician manipulates a catheter inside a patient's body, the physician often rotates the catheter about the catheter's longitudinal axis. In some catheter types, however, one direction of rotation (clockwise or counterclockwise) may be recommended, while the opposite direction should be avoided. For example, some lasso catheters have a hook-like, curved distal end in a plane that is approximately perpendicular to the longitudinal axis of the catheter. In a catheter of this sort, one direction of rotation may cause the distal end to engage or hook onto tissue, while rotation in the opposite direction is typically safer.

Embodiments of the present invention that are described herein provide methods and systems for assisting an operator (e.g., physician) in choosing the recommended direction of rotation. In some embodiments, a processor senses the direction of rotation applied to the distal end of the catheter, for example using a position sensor fitted in the catheter. The processor determines whether or not the catheter is being rotated in the recommended direction, and notifies the operator accordingly.

For example, the processor may display an indication of the sensed rotation direction on a monitor display or other output device. Additionally or alternatively, the processor may produce a visual and/or audible indication as to whether the sensed direction of rotation is the recommended direction. Using such indications, the operator is able to choose the direction of rotation so as to reduce the risk of tissue damage by the catheter and/or disruption of the catheterization procedure.

In other disclosed embodiments, the processor detects events in which the tip of the catheter's distal end is entangled or hooked onto tissue, and generates an appropriate alert. The processor typically detects such an event by identifying a change in the shape of the catheter, e.g., by detecting a change in the distance between position sensors fitted in the distal end.

System Description

Figure 1:
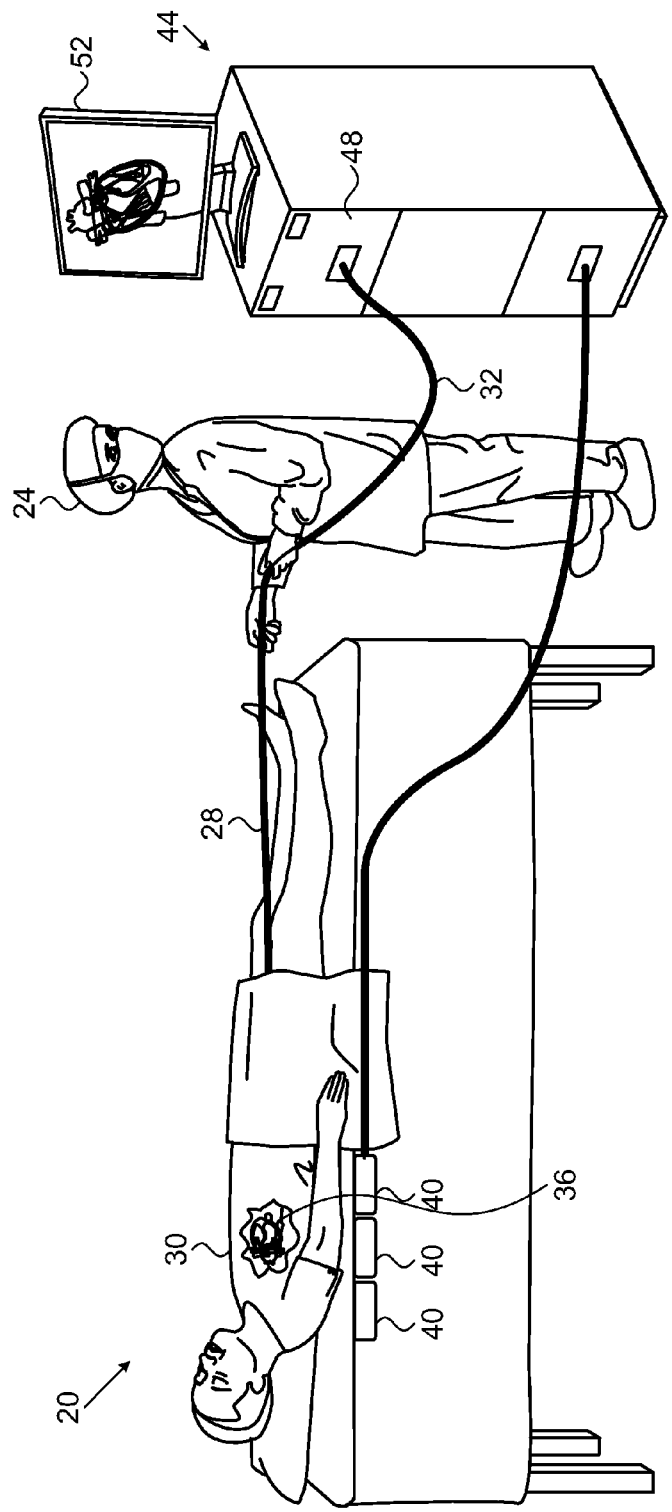
FIG. 1 is a schematic, pictorial illustration of a system for cardiac catheterization that uses position tracking, in accordance with an embodiment of the present invention.

FIG. 1 is a schematic, pictorial illustration of a system 20 for cardiac catheterization that uses position tracking, in accordance with an embodiment of the present invention. In the present example, system 20 uses magnetic position tracking. Alternatively, however, system 20 may use other suitable position tracking technologies, such as impedance-based position tracking. System 20 may be based, for example, on the CARTO™ system, produced by Biosense-Webster Inc. (Diamond Bar, Calif.). In system 20, a physician 24 (or other operator) inserts a catheter 28 (or other elongated probe) into the body of a patient 30.

Catheter 28 has a proximal end that is handled by the physician, and a distal end 36 that is navigated through the patient body. The physician moves the distal end of the catheter by manipulating the proximal end. In particular, the physician may rotate the proximal end about the longitudinal axis of the catheter, and this rotation is in turn applied to the distal end.

In the present example, distal end 36 has a lasso shape. In a typical lasso catheter, the distal end has an end section that is formed so as to define an arc that is oriented obliquely relative to the longitudinal axis of the catheter. One or more electrodes, e.g., potential sensing electrodes and/or ablation electrodes, may be disposed along the end section. Lasso catheters may be used, for example, for sensing electrical potentials at multiple points that lie on an arc surrounding an anatomical structure, such as the ostium of a pulmonary vein, and/or for ablating tissue along such an arc.

Example lasso catheters are described in U.S. patent application Ser. No. 12/649,417, filed Dec. 30, 2009; and in U.S. patent application Ser. No. 12/975,787, filed Dec. 22, 2010, which are assigned to the assignee of the present patent application and whose disclosures are incorporated herein by reference.

Catheter 28 is connected to a control console 44 using a cable 32. In the embodiment described herein, catheter 28 is inserted into the patient's heart and used for ablation and/or for creating electrophysiological maps of one or more heart chambers. Alternatively, catheter 28 may be used, mutatis mutandis, for other therapeutic and/or diagnostic purposes in the heart or in other body organs.

In the example of FIG. 1, console 44 uses magnetic position sensing to determine position coordinates of distal end 36 inside the heart. (As noted above, the disclosed techniques are not limited to magnetic position tracking. In alternative embodiments, console 44 may use any other suitable position tracking technique, for example impedance-based techniques, to track distal end 36.)

To determine the position coordinates, a driver circuit in console 44 drives field generators 40 to generate magnetic fields within the body of patient 30. Typically, field generators 40 comprise coils, which are placed at known positions below the patient's torso. One or more magnetic position sensors (not shown in the figure) within distal end 36 of catheter 28 generate electrical signals in response to these magnetic fields.

A processor 48 in console 44 processes these signals in order to determine the position coordinates of distal end 36, typically including both location and orientation coordinates. Magnetic position tracking methods of this sort are described in detail in U.S. Pat. Nos. 5,391,199, 6,690,963, 6,484,118, 6,239,724, 6,618,612 and 6,332,089, in PCT International Publication WO 96/05768, and in U.S. Patent Application Publications 2002/0065455, 2003/0120150 and 2004/0068178, whose disclosures are all incorporated herein by reference.

Based on the signals received from catheter 28, processor 48 drives a display 52 to present physician 24 with a map of cardiac electrophysiological activity, as well as providing visual feedback regarding the position of distal end 36 in the patient's body and status information and guidance regarding the procedure that is in progress.

Processor 48 typically comprises a general-purpose computer, with suitable front end and interface circuits for receiving signals from catheter 28 and controlling the other components of console 44. Processor 48 may be programmed in software to carry out the functions that are described herein. The software may be downloaded to processor 48 in electronic form, over a network, for example, or it may be provided on non-transitory tangible media, such as optical, magnetic or electronic memory media. Alternatively, some or all of the functions of processor 48 may be carried out by dedicated or programmable digital hardware components.

Recommended and Non-Recommended Rotation Directions of a Lasso Catheter

Figure 2:
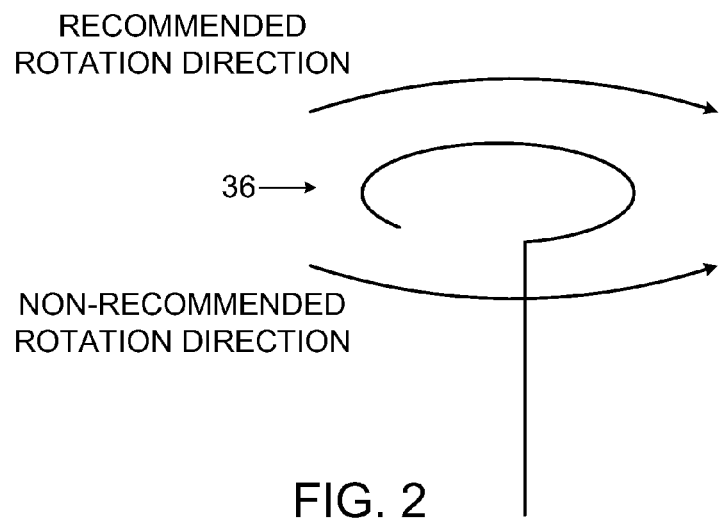
FIG. 2 is a diagram showing recommended and non-recommended directions of rotation of a lasso catheter, in accordance with an embodiment of the present invention.

FIG. 2 is a diagram showing recommended and non-recommended directions of rotation of a lasso catheter, in accordance with an embodiment of the present invention. The figure shows distal end 36 of catheter 28, which has a hook-like shape. The two possible directions of rotation about the longitudinal axis of the catheter are marked with arrows. One direction of rotation of distal end 36 is defined as a recommended direction that should be used whenever possible. The opposite direction of rotation is defined as a non-recommended direction that should be avoided as much as possible.

In the example of FIG. 2, the bottom arrow marks the non-recommended direction of rotation. Because of the shape of distal end 36, rotating the catheter in this direction may cause the tip of the distal end to hook or engage onto tissue. As a result, damage may be caused to the tissue and/or the catheter, and the catheterization procedure may be disrupted. The top arrow marks the recommended direction of rotation. Rotating the catheter in this direction is likely to be safe and free of the above-described complications.

The distal end configuration of FIG. 2 is chosen purely by way of example. In alternative embodiments, the disclosed techniques can be used with any other suitable catheter having recommended and non-recommended directions of rotation for any reason. For example, a catheter having a semi-rigid crescent-shaped distal end, or a catheter whose distal end comprises multiple arms, may entangle in tissue unless rotated in a particular recommended direction.

Notification of Non-Recommmended Catheter Rotation

Figure 3:
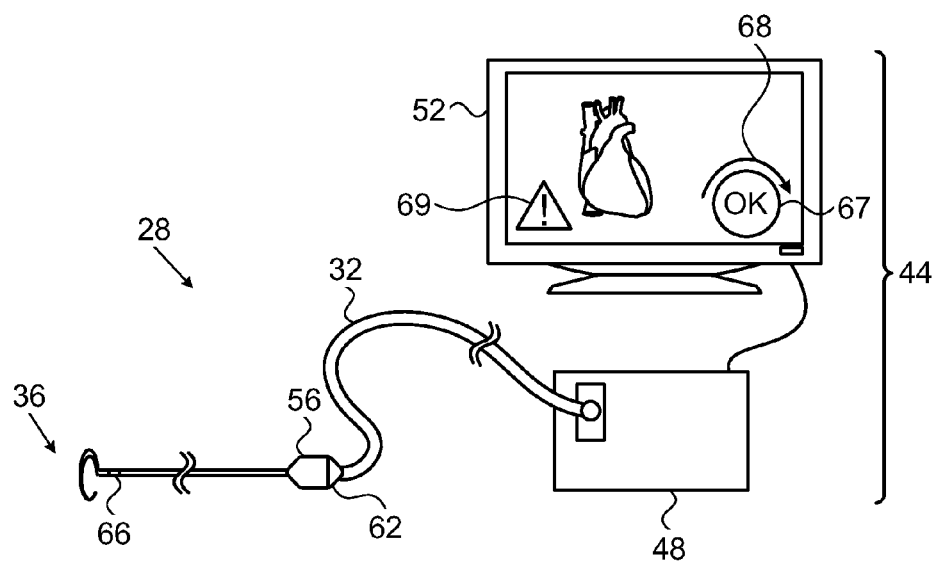
FIG. 3 is a schematic pictorial view of a system for cardiac catheterization, in accordance with an embodiment of the present invention.

FIG. 3 is a schematic, pictorial illustration of certain elements of system 20, in accordance with an embodiment of the present invention. FIG. 3 shows catheter 28 and some of console 44 in greater detail. In the present embodiment, a handle 56 is fitted at the proximal end of catheter 28. The handle is used for maneuvering the catheter by the physician, and in particular for rotating the catheter about its longitudinal axis. A connector 62 connects catheter 28 to cable 32. A magnetic position sensor 66 is fitted in distal end 36 of catheter 28, in order to carry out magnetic position tracking of the distal end by system 20, as explained above. Sensor 66 is typically fitted at or near the end of the catheter shaft, i.e., at the root of the catheter distal end.

In some embodiments, processor 48 senses the rotation that the physician applies to catheter 28. In an example embodiment, processor 48 senses the rotation based on the signals produced by magnetic position sensor 66 in the distal end. In a typical application of this sort, system 20 measures the location and orientation coordinates of distal end 36 using the magnetic position tracking methods described above. In particular, processor 48 tracks the orientation of the distal end based on the signals produced by sensor 66, and calculates the rotation angle or the rate of rotation of the catheter.

In an alternative embodiment, sensor 66 comprises an acceleration sensor. In this embodiment, the signals are indicative of the angular acceleration of the catheter about its longitudinal axis. Processor 48 processes (e.g., integrates) these signals so as to estimate the rotation angle or rate of rotation applied to the catheter.

In alternative embodiments, processor 48 may sense the catheter rotation based on inputs from two or more sensors, e.g., based on multiple sensors that are disposed along the lasso loop of the distal end. Such sensors may comprise simple (e.g., single-axis) sensors that do not necessarily each produce rotation information.

Further alternatively, processor 48 may measure or estimate the rotation applied to catheter 28 based on any other suitable sensor and using any other suitable method, e.g., by measuring the impedance between each of the lasso electrodes and patches attached to the patient body. Note that the disclosed techniques are in no way limited to use in magnetic position tracking systems such as system 20. For example, the methods described herein can be used with an acceleration sensor at the proximal end or at the distal end, without a position tracking system of any kind.

Based on the sensed rotation, processor 48 notifies the physician whether or not the catheter is being rotated in the recommended or in the non-recommended direction. The identification of one rotation direction as recommended and the other as non-recommended is typically predefined in processor 48. In some embodiments, processor 48 presents an indication of the sensed direction of rotation to physician 24. In some embodiments, processor 48 indicates whether or not the present direction of rotation is the recommended direction.

In the example embodiment of FIG. 3, processor 48 displays on display 52 an alphanumeric field 67 showing "OK" when the catheter is rotated in the recommended direction, and "WRONG" when the catheter is rotated in the non-recommended direction. In another embodiment, processor 48 displays an arrow 68, whose direction indicates the direction of rotation of the catheter. In an example embodiment, the arrow is displayed in a manner that indicates whether the direction of rotation is recommended or not. For example, an arrow indicating the non-recommended direction may be colored red, while an arrow indicating the recommended direction may be colored green. Alternatively, processor 48 may present any other suitable indication, e.g., using a suitable alphanumeric or graphical indication.

In some embodiments, processor 48 generates an alert when the catheter is rotated in the non-recommended direction. Any suitable type of alert and any suitable output device for generating the alert can be used, e.g., displaying a visual alert on display 52 or sounding an audible alert using a loudspeaker or other audio output device. Based on the indication generated by processor 48, physician 24 is able to prefer the recommended direction of rotation whenever possible.

In some embodiments, processor 48 detects events in which the tip of distal end 36 becomes entangled with tissue (either because the catheter was rotated in the non-recommended direction or for any other reason). Example methods for detecting catheter tip entanglement are described further below. Upon detecting tip entanglement, processor 48 issues an alert to the physician. Any suitable type of alert and any suitable type of output device can be used for this purpose, such as the examples given above for the rotation direction alert. In the example of FIG. 3, processor 48 displays a warning icon 69 on display 52.

Additional aspects of measuring catheter rotation and indicating the rotation to an operator are addressed in U.S. patent application Ser. No. 12/851,085, entitled "Catheter Entanglement Indication," which is assigned to the assignee of the present patent application and whose disclosure is incorporated herein by reference.

Detection and Notification of Catheter Tip Entanglement

In some cases, the tip of distal end 36 may become stuck or engaged in tissue, an event that may risk the patient and/or the catheter. For example, the tip of a lasso catheter may hook onto the heart's papillary muscle. As another example, one or more tips of a multi-arm catheter may hook onto the heart's papillary muscle or a heart valve. Events of this sort are all referred to herein as "tip entanglement." In some embodiments, processor 48 detects tip entanglement by identifying a change or abnormality in the shape of the catheter distal end.

Figure 4A:
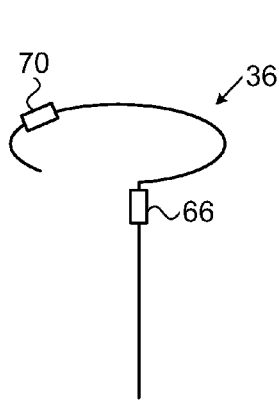
FIGS. 4A and 4B are diagrams showing a scheme for detecting tip entanglement in a lasso catheter, in accordance with an embodiment of the present invention.
Figure 4B:
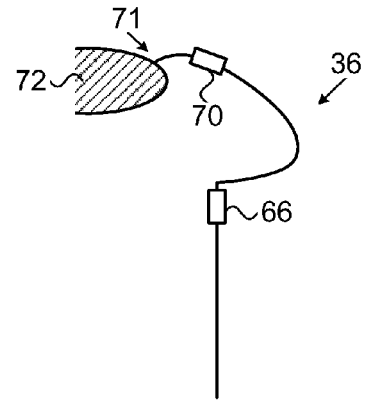

FIGS. 4A and 4B are diagrams showing a scheme for detecting entanglement of distal end 36 in tissue, in accordance with an embodiment of the present invention. FIG. 4A shows the normal shape of distal end 36. FIG. 4B shows distal end 36 when a tip 71 of the distal end is entangled in tissue 72.

As can be seen in the figure, the tip entanglement causes a change or abnormality in the shape of the lasso loop. Processor 48 typically detects the tip entanglement by identifying this abnormality, i.e., by identifying that the shape of the distal end deviates from the normal baseline shape by more than a tolerable amount.

In an example embodiment, a position sensor 70 is fitted on the lasso loop, typically more than half-way toward tip 71. In this embodiment, processor 48 measures the positions of sensors 66 and 70 using the methods described above, and calculates the distance between the two sensors. If the distance exceeds a reference distance (e.g., the distance under normal conditions as seen in FIG. 4A) by more than a predefined threshold, processor 48 concludes that the distal tip is entangled.

As another example, processor 48 may detect tip entanglement by identifying that the lasso loop deviates from a single plane, e.g., by identifying that the lasso electrodes (or position sensors fitted along the lasso loop) are not all on the same plane. These conditions are typically regarded as indicating entanglement provided that the catheter is out of its sheath, i.e., in its expanded position.

One possible way for processor 48 to detect that the catheter's lasso loop deviates from a single plane is to find a point on the lasso loop that is closest to tip 71, excluding the most distal section (e.g., half) of the loop from the search. If the distance between this point and the catheter tip is above some threshold, processor may conclude that the loop deviates from a single plane.

In alternative embodiments, processor 48 may detect tip entanglement using any other suitable method. As explained above, in response to detecting tip entanglement processor 48 typically issues an alert.

Figure 5:
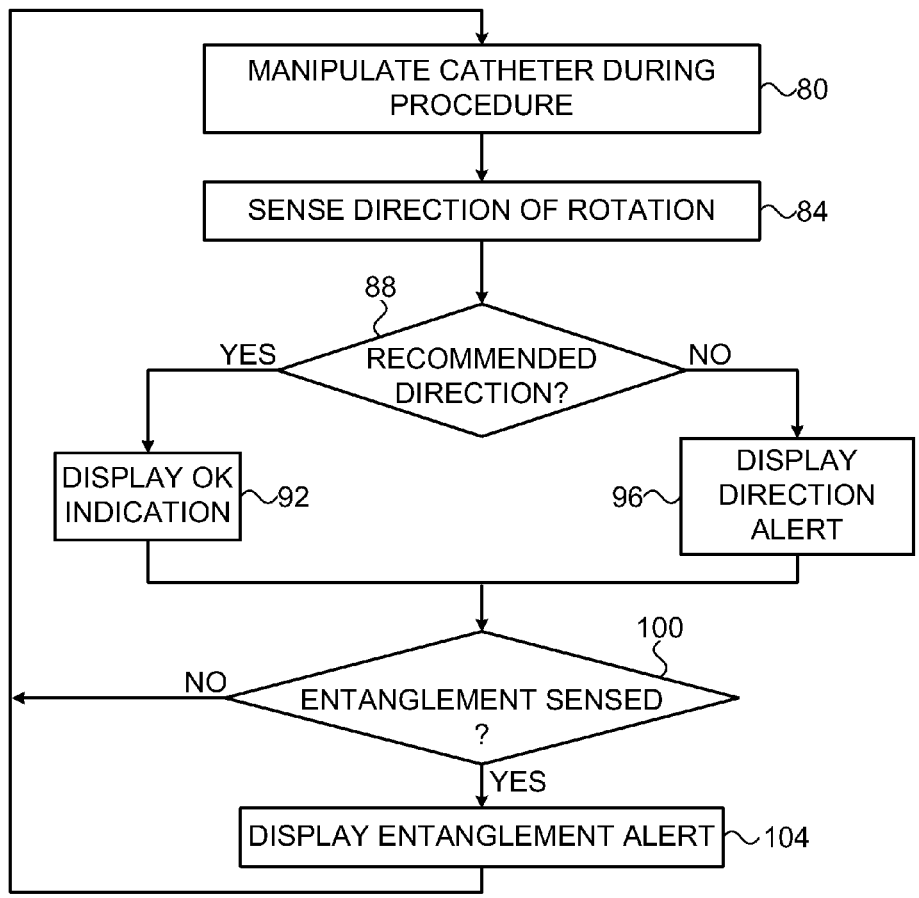
FIG. 5 is a flow chart that schematically illustrates a method for controlling rotation of a catheter, in accordance with an embodiment of the present invention.

FIG. 5 is a flow chart that schematically illustrates a method for preventing rotation of a catheter in a non-recommended direction, in accordance with an embodiment of the present invention. The method begins with physician 24 maneuvering catheter 28 in the body of patient 30 as part of a medical procedure, at a catheter manipulation step 80. In particular, the physician applies rotation to the catheter with respect to the catheter's longitudinal axis.

Processor 48 senses the direction of the rotation applied to the catheter during the procedure, at rotation sensing step 84. Any suitable measurement method and sensor, such as the schemes described above, can be used.

Processor 48 checks whether the sensed direction of rotation is the recommended direction or the non-recommended direction, at a direction checking step 88. If the sensed rotation is in the recommended direction, processor 48 displays an "OK" indication to physician 24 on display 52, at a recommended direction indication step 92. If, on the other hand, the sensed rotation is in the non-recommended direction, processor 48 displays an alert indication, at a non-recommended direction indication step 96.

Processor 48 then checks whether tip 71 of distal end 36 is entangled in tissue, at an entanglement checking step 100. Processor 48 may detect tip entanglement, for example, by measuring the distance between sensors 66 and 70 (FIGS. 4A and 4B). If no tip entanglement is detected, the method loops back to step 80 above. If tip entanglement is detected at step 100, processor 48 issues an entanglement alert, at an entanglement alerting step 104. The method then loops back to step 80 above.

In some embodiments, processor 48 detects that the lasso catheter is rotated in the non-recommended direction using the following method: The Lasso loop is approximated by a plane. A normal to this plane is the axis around which the lasso rotation is measured and filtered. For a counter-clockwise (CCW) loop, the non-recommended rotation direction can be defined as the difference between the current value of the rotation angle, and the minimal value of the rotation angle until the present time. If this difference exceeds some positive threshold, processor 48 concludes that the catheter is being rotated in the non-recommended direction. For a clockwise (CW) loop, the non-recommended rotation direction can be defined as the difference between the current value of the rotation angle, and the maximal value of the rotation angle until the present time. If this difference is below some negative threshold, processor 48 concludes that the catheter is being rotated in the non-recommended direction.

In some embodiments, system 20 comprises an electrophysiological mapping system that enables the physician to generate maps of the four heart chambers (i.e., the two atria and the two ventricles), and indicate the catheter location within the heart. Some catheters are designed for use only in the atria, and it is highly recommended not to place them in a ventricle. When using such catheters, processor 48 of system 20 may issue an alert when the measured catheter position indicates that it is located in a ventricle.

Although the embodiments described herein mainly address lasso catheters, the methods and systems described herein can also be used with other types of medical probes having recommended and non-recommended directions of rotation. Although the embodiments described herein refer mainly to rotation of a medical probe, the disclosed techniques can be used for recommending the direction of rotation in other devices.

Although the embodiments described herein refer mainly to detecting deformation in a lasso loop of a catheter in order to identify entanglement of the lasso tip, the disclosed techniques can be used to detect deformation of various other medical instruments, such as in procedures that involve insertion of flexible medical instruments into the heart, the spine, the epidural space, the brain or any other organ. For example, the disclosed techniques can be used to verify the direction of a temperature probe, which is inserted into the esophagus in order to measure heating of the side of the esophagus that is adjacent to the heart. In this application it is important to verify that the probe is indeed pointed toward the heart.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising: providing an elongated probe having a longitudinal axis and a distal end, and capable of rotation of the distal end about the longitudinal axis in mutually opposite first and second directions, the distal end comprising an end section formed to define an arc that is oriented obliquely to the longitudinal axis;
   while an operator manipulates the probe within a body of a patient, automatically sensing the rotation that is applied to the distal end; and
   automatically detecting an abnormality in the shape of the distal end of the elongated probe and issuing an alert to the operator upon sensing that the rotation is in the second direction, but not when sensing that the rotation is in the first direction, the alert allowing the operator to prevent the distal end of the elongated probe from engaging onto tissue and preventing damage to the tissue.

2. The method according to claim 1, wherein the distal end comprises a hook-shaped curve in a plane that is oriented obliquely with respect to the longitudinal axis.

3. The method according to claim 1, wherein the probe comprises a lasso cardiac catheter.

4. The method according to claim 1, wherein automatically sensing the rotation comprises receiving a signal from a sensor coupled to the probe, and determining the rotation based on the signal.

5. The method according to claim 4, wherein receiving the signal comprises accepting the signal from a position sensor that generates the signal responsively to an externally-generated magnetic field.

6. The method according to claim 4, wherein receiving the signal comprises accepting the signal from an acceleration sensor that generates the signal responsively to an angular acceleration of the probe.

7. The method according to claim 4, wherein the sensor is coupled to the distal end of the probe.

8. The method according to claim 1, wherein sensing the rotation comprises measuring an impedance between at least one sensor coupled to the distal end and one or more electrodes attached to the body of the patient, and calculating the rotation based on the impedance.

9. The method according to claim 1, wherein issuing the alert comprises displaying a visual alert on a monitor display viewed by the operator.

10. The method according to claim 1, wherein issuing the alert comprises sounding an audible alarm to the operator.

11. The method according to claim 1, and comprising detecting an entanglement of the distal end with tissue in the body, and issuing a notification of the entanglement to the operator.

12. The method according to claim 11, wherein detecting the entanglement comprises detecting a deviation of a shape of the distal end from a reference shape.

13. The method according to claim 1, wherein the probe is designated for operation in atria of a heart of the patient, and comprising measuring a location of the probe and alerting the operator upon detecting that the probe is located in a ventricle of the heart.

14. An apparatus, comprising: a processor, which is connected to an elongated probe that has a longitudinal axis and a distal end and is capable of rotation of the distal end about the longitudinal axis in mutually opposite first and second directions, the distal end comprising an end section formed to define an arc that is oriented obliquely to the longitudinal axis, wherein the processor is configured to automatically sense the rotation that is applied to the distal end while an operator manipulates the probe within a body of a patient, and to automatically detect an abnormality in the shape of the distal end of the elongated probe and to issue an alert upon sensing that the rotation is in the second direction, but not when sensing that the rotation is in the first direction; and an output device, which is configured to present the alert to the operator, the alert allowing the operator to prevent the distal end of the elongated probe from engaging onto tissue and preventing damage to the tissue.

15. The apparatus according to claim 14, wherein the distal end comprises a hook-shaped curve in a plane that is oriented obliquely with respect to the longitudinal axis.

16. The apparatus according to claim 14, wherein the probe comprises a lasso cardiac catheter.

17. The apparatus according to claim 14, wherein the processor is configured to automatically sense the rotation by receiving a signal from a sensor coupled to the probe, and determining the rotation based on the signal.

18. The apparatus according to claim 17, wherein the processor is configured to receive the signal from a position sensor that generates the signal responsively to an externally-generated magnetic field.

19. The apparatus according to claim 17, wherein the processor is configured to receive the signal from an acceleration sensor that generates the signal responsively to an angular acceleration of the probe.

20. The apparatus according to claim 17, wherein the sensor is coupled to the distal end of the probe.

21. The apparatus according to claim 14, wherein the processor is configured to measure an impedance between at least one sensor coupled to the distal end and one or more electrodes attached to the body of the patient, and to calculate the rotation based on the impedance.

22. The apparatus according to claim 14, wherein the processor is configured to detect an entanglement of the distal end with tissue in the body, and to issue a notification of the entanglement to the operator.

23. The apparatus according to claim 22, wherein the processor is configured to detect the entanglement by detecting a deviation of a shape of the distal end from a reference shape.

24. The apparatus according to claim 14, wherein the probe is designated for operation in atria of a heart of the patient, and wherein the processor is configured to measure a location of the probe, and to alert the operator upon detecting that the probe is located in a ventricle of the heart.

* * * * *